United States Patent [19]

Pazdernik

[11] Patent Number: 4,753,649
[45] Date of Patent: Jun. 28, 1988

[54] FILM REINFORCEMENT FOR DISPOSABLE DIAPERS HAVING REFASTENABLE TAPES

[75] Inventor: Patrick A. Pazdernik, Neenah, Wis.

[73] Assignee: Kimberly-Clark Corporation, Neenah, Wis.

[21] Appl. No.: 32,841

[22] Filed: Mar. 31, 1987

[51] Int. Cl.⁴ .............................................. A61F 13/16
[52] U.S. Cl. ................................................. 604/389
[58] Field of Search ...................... 604/389, 390, 385.1

[56] References Cited

U.S. PATENT DOCUMENTS

| | | |
|---|---|---|
| 3,610,244 | 10/1971 | Jones, Sr. . |
| 3,669,822 | 6/1972 | Cowen .................................. 161/130 |
| 3,867,940 | 2/1975 | Mesek et al. . |
| 3,900,031 | 8/1975 | Endres et al. ........................ 604/390 |
| 4,210,144 | 7/1980 | Sarge III, et al. . |
| 4,296,750 | 10/1981 | Woon et al. ......................... 604/390 |
| 4,436,520 | 3/1984 | Lipko et al. ......................... 604/385 |
| 4,655,761 | 4/1987 | Grube et al. ........................ 604/389 |

FOREIGN PATENT DOCUMENTS

| | | |
|---|---|---|
| 80647 | 6/1983 | European Pat. Off. . |
| 148587 | 7/1985 | European Pat. Off. . |
| 2129689 | 5/1984 | United Kingdom . |
| 2135568 | 9/1984 | United Kingdom . |

*Primary Examiner*—John D. Yasko
*Attorney, Agent, or Firm*—Paul Yee

[57] ABSTRACT

An article, which includes a refastenable adhesive tape fastening system, comprises an adhesive tape tab which has a peel force value of at least about 11.7 N, and a substrate layer which is composed of a nonwoven synthetic polymer material. The substrate layer has a matte finish, and has a tensile load capacity which is substantially unable to prevent tearing thereof when the tape tab is peeled from adhesive contact with the substrate layer. A reinforcement layer has a first major surface bonded to the substrate layer, and has a second major surface which is appointed for adhesive bonding with the adhesive tape tab. The reinforcement layer also has a matte finish and a yield tensile strength of at least about 15 MPa. The reinforcement layer and substrate layer thereby form a composite, reinforced substrate having a composite tensile load capacity capable of withstanding the peeling removal of the adhesive tape tab substantially without tearing.

26 Claims, 2 Drawing Sheets

FILM REINFORCEMENT FOR DISPOSABLE DIAPERS HAVING REFASTENABLE TAPES

TECHNICAL FIELD

The present invention pertains to articles which employ adhesive tape fastening arrangements for securement onto the body of a wearer. More particularly, the present invention relates to absorbent articles employing pressure-sensitive adhesive tape tabs which can be released and refastened a plurality of times onto a target region of the article.

BACKGROUND OF THE INVENTION

Convention garment articles, particularly limited-use disposable articles, such as disposable caps, gowns, diapers, incontinence garments and the like, have employed pressure-sensitive tape tabs to fasten the garment on the wearer. With these garments, it has been desirable to selectively disengage the tape fastener for various purposes. For example, a refastenable tape tab would allow a refitting of a disposable diaper on an infant, and would more readily allow a person to check for a soiled condition of the diaper. If the diaper is not soiled, the tapes could be refastened and a usable garment would not be wasted.

The materials employed for limited use garments are typically thin and do not have sufficient strength to withstand peeling forces generated by the removal of the tape fasteners. The garment material can tear and residual material can remain attached to the adhesive layer on the tape tab. As a result, the tape tab may be unusable or the garment may be too badly damaged for further use.

Various techniques have been employed to reinforce the fastening tape target area of the garment material. For example, U.S. Pat. No. 3,900,031 issued Aug. 19, 1975 to D. Endres, et al. describes a disposable diaper having a reinforced waistband. The diaper includes a facing sheet, backing sheet and a supplemental plastic strip which are heat sealed together at the diaper edge adjacent the end of an absorbent filler to provide a reinforced area at the edge of the waistband where the pressure-sensitive fastening tape is attached. In addition, U.S. Pat. No. 4,296,750 issued Oct. 27, 1981 to L. S. Woon, et al. describes a disposable diaper in which a hot melt adhesive layer is applied onto an impermeable film backing to provide a composite structure having high resistance to tearing.

Other refastenable tape systems have employed multi-piece tapes which include a fastening tape portion and a target tape portion. Once the target tape portion has been positioned and secured onto a selected portion of a garment, the fastening tape can then be repeatedly removed and readhered. For example, see European patent application EP No. 0148 587 A2 published July 17, 1985 with the inventor listed as P. Pape.

U.K. patent application GB No. 2 135 568 A describes a disposable diaper having coded zones to enable the adjustment of a diaper to the infant and/or check the need for changing the size of a diaper in relation to the infant's weight.

Other refastenable tape systems have incorporated a plastic layer or strip affixed to an outer surface of a garment to provide a strengthened fastening zone. For example, see U. K. patent application GB No. 2 129 689 A published May 23, 1984 with L. Widlund listed as inventor. In addition, see European patent application EP No. 0 080 647 A1 published June 8, 1983 with R. de Jonckheere, et al. listed as inventors.

Conventional refastenable tape systems, such as those described above, have not been completely satisfactory. Multi-piece tape systems, such as those described in EP No. 0 148 587 A2 require a precise balance between the adhesive force which secures the target tape member to the outer surface of the garment and the adhesive force which secures the fastening tape tab onto the target member. If the adhesive force between the fastening tape and the target member is too high, the target member may peel or tear from the garment. Also, the target member is relatively small and allows only a small amount of repositioning of the fastening tape tab once the target member is affixed onto the garment.

Garment configurations in which a reinforcement layer is attached to the inner or outer surface of the garment outer layer have undesirably degraded the appearance of the garment. When affixed to the inner side of the garment outer cover layer, the bonding or adhesive pattern can undesirably show through the cover layer or can physically distort the cover layer. When affixed to the outer surface of the garment cover layer, there can be an unattractive contrast between the reinforcement layer and the remainder of the garment outer cover. The reinforcement layer is typically composed of an oriented, relatively high-strength film which presents a glossy, shiny surface. The high-strength film can be expensive, and its shiny appearance can undesirably contrast with the matte finish of the remainder of the garment and provide a harsh plastic appearance which consumers often find objectionable. In addition, conventional refastenable tape systems have not provided a sufficiently secure adhesive attached between the fastening tape and the attachment target zone of the garment. As a result, premature releasing of the fastening tape tab has remained a problem.

BRIEF DESCRIPTION OF THE INVENTION

The present invention provides a distinctive article comprising an adhesive tape tab which has a peel force value of at least about 11.7 N (newton) and a substrate layer composed of material having a matte finish and a tensile load capacity which is substantially unable to prevent tearing thereof when the tape tab is peeled from adhesive contact from the substrate layer. A reinforcement layer has a first major surface which is bonded to the substrate layer and a second major surface which is appointed for adhesive bonding with the adhesive tape tab. The reinforcement layer has a matte finish and a yield tensile strength of at least about 15 MPa (megapascal). The reinforcement layer and the substrate layer thereby form a composite, reinforced substrate having a tensile load capacity capable of withstanding the peeling removal of the adhesive tape tab substantially without tearing or permanently deforming.

The structure of the present invention advantageously provides an aggressive refastenable tape system which has a high adhesion value to a selected fastening target area. In addition, the adhesive tape tab can be readily removed from the target area substantially without tearing the garment. As a result, when compared to conventional refastenable tape systems, the structure of the present invention can be less susceptible to unintensional release, have lower material costs and can maintain a desired matte finish and pleasing appearance over the entire outer surface of the garment.

BRIEF DESCRIPTION OF THE DRAWINGS

The present invention will be more fully understood and further advantages will become apparent when reference is made to the following detailed description of the invention and the drawings, in which.

DETAILED DESCRIPTION OF THE INVENTION

The following detailed description of the present invention will be made in the context of an absorbent diaper article. However, it will be readily apparent to a person having ordinary skill in the art that the described structures would be suitable for use in fastening systems for other articles such as gowns, caps, packages, feminine care articles, incontinence garments and the like.

Figure 1:
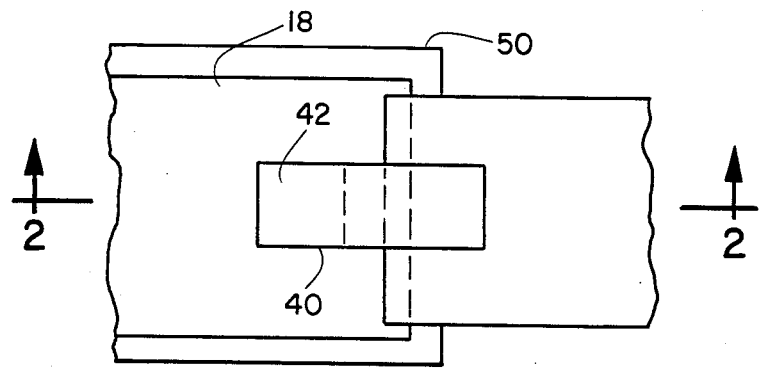
FIG. 1 shows a representative top plan view of an article incorporating a refastenable tape securement system.
Figure 2:
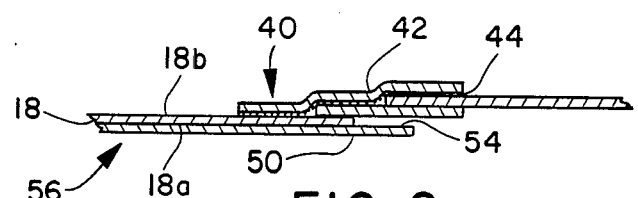
FIG. 2 representatively shows a cross-sectional view taken along line 2—2 of FIG. 1.

With reference to FIG. 1, the article of the present invention incorporates a distinctive adhesive tape fastening system comprising an adhesive tape tab 40 which has a peel force value of at least about 11.7 N (about 2.64 lb-force), and a substrate layer 50 composed of a nonwoven synthetic polymer material. The substrate layer has a matte finish and has a tensile load capacity which is substantially unable to prevent tearing thereof when tape tab 40 is peeled from adhesive contact with substrate layer 50. A reinforcement layer 18 has a first major surface 18a which is bonded to an outwardly facing surface 54 of substrate layer 50, and has a second major surface 18b which is appointed for adhesive bonding with tape tab 40. The reinforcement layer also has a matte finish and a tensile strength of at least about 15 MPa (about 2200 psi). Reinforcement layer 18 and substrate layer 50, in combination, thereby form a composite reinforced substrate 56 which has a composite tensile load capacity capable of withstanding the peeling removal of adhesive tape tab 40 therefrom substantially without tearing or delaminating.

As employed in the description of the present invention, the term, tensile strength, is intended to designate the yield tensile strength of the material. The yield tensile strength is the stress at which the material first begins to plastically deform to develop a permanent deformation. Similarly, the term, tensile load capacity, is intended to designate the tensile load at which a sample of material first begins to yield and plastically deform.

Figure 3:
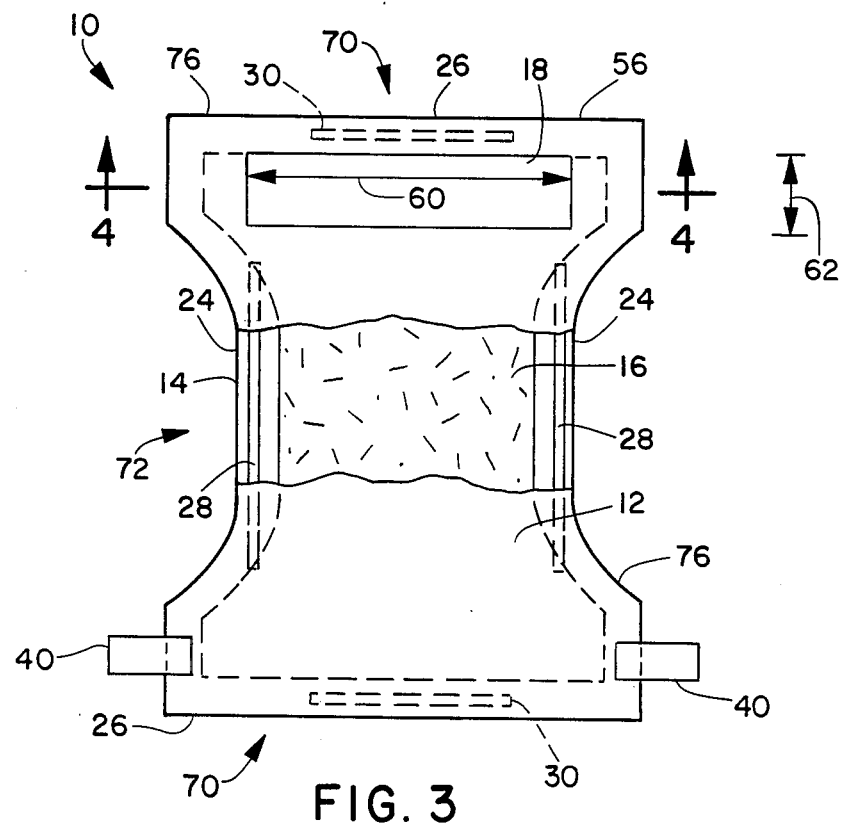
FIG. 3 shows a representative top plan view of an absorbent diaper article incorporating the refastenable tape structure of the present invention.
Figure 4:
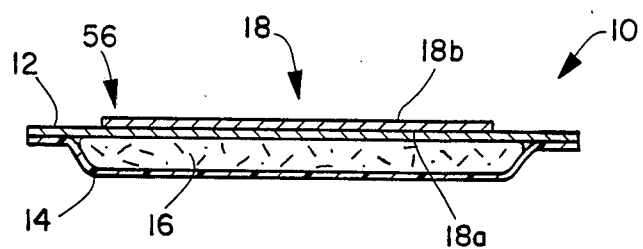
FIG. 4 representatively shows a cross-sectional view taken along line 4—4 of FIG. 3.
Figure 5:
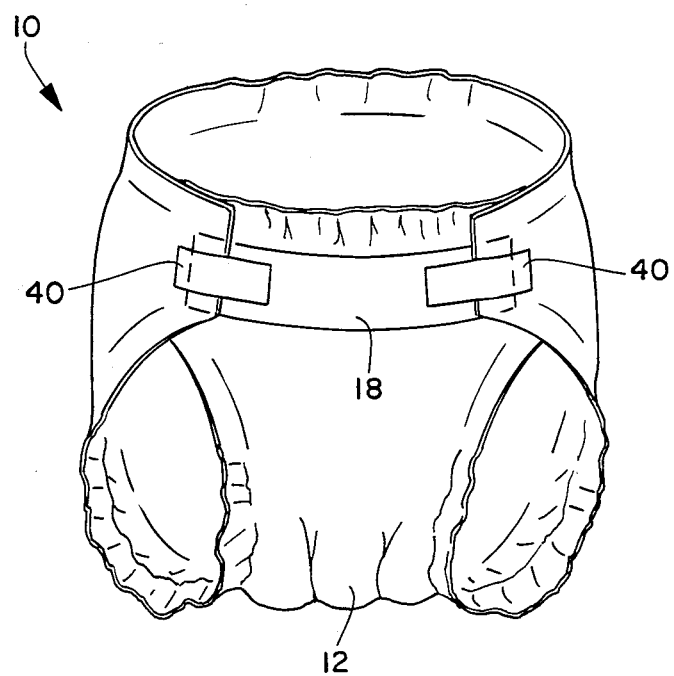
FIG. 5 representatively shows the approximate configuration of a diaper when placed on a wearer.

In a more particular embodiment shown in FIG. 3, an absorbent article, such as disposable diaper article 10, comprises a backsheet layer 12 composed of a nonwoven synthetic material which defines and delimits waistband sections 70 at each longitudinal end thereof, and defines and delimits an intermediate section 72 interconnecting the waistband sections. Backsheet 12 also has a matte finish, a thickness and a selected tensile strength. A substantially liquid-permeable liner sheet 14 is superposed in facing relation with backsheet layer 12, and an absorbent body 16 is located between the backsheet layer and the liner sheet. An adhesive tape tab 40 is connected to each of two laterally opposed, side portions of at least one waistband section 70 of the backsheet layer. The adhesive tape tab has a peel force value which measures at least about 11.7 N and which is capable of tearing the backsheet when the tab is peeled from adhesive contact therewith. A reinforcement layer 18 has a first major surface 18a, which is bonded to the backsheet layer 12, and has a second major surface 18b, which is appointed for bonding with the adhesive tape tab 40. The reinforcement layer has a matte finish and a tensile strength of at least about 15 MPa ( about 2200 psi). The combination of reinforcement layer 18 and backsheet layer 12 thereby form a composite, reinforced backsheet having a tensile strength capable of withstanding the peel force value of adhesive tape tab 40 substantially without tearing or delaminating.

As illustrated by FIG. 3, the diaper liner sheet and absorbent body each have waistband sections interconnected by an intermediate section, and in the shown embodiment, the intermediate section of diaper 10 is narrower than the waistband sections. Diaper 10 thus has a generally hourglass or I-shape planform with the waistband sections 70 defining ear sections 76 extending oppositely along the lateral, cross-direction of the garment. Two ear sections at one waistband of the diaper include adhesive tape tabs 40 for fastening the diaper on a wearer. In the shown embodiment, backsheet 12 and liner sheet 14 are essentially coterminous and extend out past the edges of absorbent body 16 to form marginal edges 24 and 26. The embodiment further includes elastic members 28 which are attached to each of the diaper side margins 24 and are configured to gather and shirr legband portions of diaper 10 to form seals or gaskets around the legs of the wearer. In addition, diaper 10 can include waist elastic members 30 secured to one or more of the end margins 26 to gather and shirr the waistband sections of the diaper.

The various components of diaper 10 are assembled together employing conventional techniques. For example, the components may be attached to one another employing thermal or sonic bonds, or mechanical fasteners, such as snaps or clips. Alternatively, the components can be attached with adhesives, such as hot melt pressure-sensitive adhesives. The adhesives can be applied by employing conventional techniques, such as by spraying droplets or filaments of the adhesive. In the shown embodiment of the invention, the components are assembled employing a plurality of generally parallel lines of hot melt pressure-sensitive adhesive oriented along the length dimension of the diaper.

Liner sheet 14 in the illustrated embodiment is typically composed of a liquid-permeable, substantially hydrophobic material, such as a spunbonded web composed of synthetic polymer filaments. Alternatively, liner sheet 14 may comprise a meltblown web or a bonded-carded-web composed of synthetic polymer filaments. Suitable synthetic polymers include, for example, polyethylene, polypropylene, polyesters, rayon and blends thereof. The topsheet has an effective pore size between fibers which readily allows the passage therethrough of liquids, such as urine and other body exudates. Optionally, the topsheet can be selectively embossed or perforated to provide discrete slits or holes extending therethrough and may be treated with a surfactant.

Absorbent body 16 typically comprises a pad composed of airlaid cellulosic fibers commonly referred to as wood pulp fluff. Conventional pads can have a density ranging from about 0.05–0.2 g/cc, and are sufficiently flexible to readily conform to the body of the wearer. Absorbent body 16 may also comprise a coform material composed of a mixture of cellulosic fibers and synthetic polymer fibers. For example, the coform material may comprise an airlaid blend of cellulosic wood fibers and meltblown polyolefin fibers, such as polyethylene or polypropylene fibers.

Absorbent body 16 may also include an effective amount of an inorganic or organic high-absorbency material to enhance the absorptive capacity of the absorbent body. For example, absorbent body 16 can include 5–95 wt % high absorbency material, and preferably includes about 10–30 wt % of the high-absorbency material. Suitable inorganic high-absorbency materials include, for example, absorbent clays and silica gels. Organic high absorbency materials can include natural materials, such as pectin, guar gum, and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacylamides, polyvinyl pyridine and the like. Other suitable polymers can include hydrolyzed acrylonitrile grafted starch, acrylic acid grafted starch and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Celanese Corporation, Allied-Colloid, and Stockhausen. Typically, the high-absorbency material is capable of absorbing at least about 15 times its weight in water, and preferably is capable of absorbing at least about 25–50 times its weight in water.

The high-absorbency material can be distributed or otherwise incorporated into absorbent body 16 employing various techniques. For example, the high-absorbency material can be substantially uniformly distributed among the fibers comprising the absorbent body. The materials can also be nonuniformly distributed within the absorbent body fibers to form a generally continuous gradient with either an increasing or decreasing concentration of high-absorbency material, as determined by observing the concentration moving from the body-side of absorbent body 16 to the outer-side of the absorbent body. Alternatively, the high-absorbency material can comprise a discrete layer separate from the fibrous material of absorbent body 16, or can comprise a discrete layer integral with the absorbent body. Absorbent body 16 can optionally include a tissue wrap to help maintain the integrity of the airlaid fibrous structure. The tissue wrap typically comprises a cellulosic material, such as a high-wet-strength tissue.

A particular embodiment of the invention includes a backsheet 12 composed of a liquid-impermeable material, such as a polymer film. For example, backsheet 12 can be composed of a polyolefin film, such as polyethylene or polypropylene. In another embodiment of the invention, backsheet 12 can be composed of a liquid impermeable, but vapor-permeable material, such as a "breathable" microporous polyethylene film.

Backsheet 12 may also comprise a polymer film which has been textured or embossed to adjust the tactile properties of the material. Alternatively, the backsheet may comprise a cloth-like, fibrous nonwoven web, or a composite web composed of different fibrous and film materials arranged to produce a cloth-like appearance. For example, the composite web of backsheet 12 may be a stretchable, elastomeric web, such as a stretch-bonded laminate. Examples of such laminated materials are set forth in U.S. patent application Ser. No. 760,437; entitled "Composite Elastomeric Material and Process for Making the Same" of J. Taylor, et al.; and U.S. patent application Ser. No. 843,428; entitled "Improved Composite Elastomeric Material and Process for Making the Same" of Daponte;

To improve consumer acceptance of the garment, the backsheet material should be thin and flexible to reduce noise and rattle when the garment is manipulated. In a preferred aspect of the invention, the backsheet material has a thickness within the range of about 0.01–0.05 mm. An alternative nonwoven fibrous backsheet can have a thickness within a range of about 0.12 to 0.64 mm. and a basis weight from about 1.6 to 6.0 grams per square meter. Consumer acceptance is further enhanced by providing a backsheet material which has a substantially nonglossy, matte finish which provides a pleasing garment-like appearance. Thin, matte-finish film materials, however, tend to be weaker than oriented film materials having a glossy finish. As a result, the backsheet material is capable of supporting only a limited tensile load, and the load bearing capacity of backsheet 12 is ordinarily unable to withstand the peeling force generated when a fastening tape tab is peeled from adhesive contact with the backsheet. The tensile strength of the material of backsheet 12 is ordinarily less than about 10.8 MPa (about 1600 psi), and typically is within the range of about 3.8–30 MPa (about 550–4400 psi).

For the purposes of the present invention, a suitable procedure for determining tensile strength is PSTC-31 employing an Instron test apparatus and a test sample measuring 1 inch (2.54 cm.) in width.

In an alternative embodiment of the invention wherein backsheet 12 comprises a fibrous nonwoven material, the nonwoven material can be characterized by a grab tensile load value. A suitable procedure for determining the grab tensile load is ASTM D-1117 employing an Instron test apparatus. Nonwoven materials which may be employed with the present invention can have a grab tensile load value within the range of about 36–113 N (8–30 lb-force) and typically have a grab tensile load of less than about 89 N (19.8 lb-force).

Taking into consideration the caliper or thickness of the backsheet material, backsheet 12 is typically capable of providing a tensile load capacity of not more than about 15 N (about 3.4 lb-force), and more typically provides a load capacity within the range of about 4.9–14.7 N (about 1.1–3.3 lb-force). In the illustrated embodiment, the backsheet has a load capacity of about 8.9 N (about 2.0 lb-force). The tensile load capacity of the material is determined with respect to a test sample having a width dimension of 1 inch (2.54 cm.), and is measured at the point at which the test sample first begins to yield and plastically deform.

Tape tab 40, in the shown embodiment, comprises a carrier member 42 and a layer 44 of adhesive bonded to the carrier member. Tape tab 40 is factory bonded to two lateral ear portions of the rear waistband section of diaper 10, and adhesive layer 44 preferably comprises a pressure-sensitive adhesive. Suitable adhesive tape tab materials are available from 3M Company of St. Paul, MN.

To provide a desired level of securement and reliability, tape tab 40 has an average peel adhesion force value of at least about 11.7 N. Preferably, the tape tab has a peel force value of at least about 15.7 N, and more preferably has a peel force value of at least about 17.6 N to provide improved performance. The peel force values are determined with respect to a 1 inch wide adhesive tape tab.

For the purposes of the present invention, the peel force value can be determined in accordance with Pressure Sensitive Tape Council procedure PSTC-1 (ASTM-D3330) modified such that the 1 inch wide adhesive tape tab being tested is peeled directly from a substrate composed of the selected reinforcement layer material.

In the standard PSTC-1 test procedure, the test sample of adhesive tape is peeled at a peel angle of 180° from a steel block substrate measuring 2.5 inches wide and 6 inches long. In the procedure modified for the purposes of the present invention, both longitudinal ends of a 2.5 inch×6 inch sample of the selected reinforcement layer are bonded to the steel block over an area measuring 1 inch×2.5 inches, leaving an unbonded intermediate region which measures 4 inches×2.5 inches. A piece of fluff pad material measuring 2.5 inches×2.5 inches and having a basis weight of 800 grams per square meter is interposed between the steel block and the intermediate region of the reinforcement layer material to better simulate actual conditions on an absorbent article. The piece of fluff pad is held in place by friction, and the intermediate region is the target test zone against which the test tape is adhesively connected. The 180° peel separation rate is set at 18 cm./sec., and the dwell time between adhering the tape tab to the test zone and peeling away the tape tab is less than 10 minutes. Peel force values are recorded each 100 microseconds during the separation. Suitable test equipment is available from MTS Systems Corporation, Minneapolis, Minn.

The relatively high peel force value incorporated into the tape fastening system of the present invention can advantageously provide more a secure fastening of a garment onto a wearer. The tape tabs are less susceptible to inadvertent release or premature release caused by a highly active wearer. Such high peel force values, however, may readily tear the backsheet material and make it difficult to provide a reliable refastenable tape system. In particular, when the backsheet is composed of a fibrous nonwoven, individual fibers can be torn away by the tape tab and contaminate the adhesive layer; when the backsheet is composed of a film material, the film can tear and separate. Tearing the backsheet material can, for example, degrade the liquid barrier function of the backsheet, and any torn pieces of backsheet material remaining attached to tape tab 40 can degrade the fastening ability of the adhesive.

To achieve a desired level of refastenability, backsheet 12 is augmented with a supplementary, reinforcement layer, such as sheet layer 18. In the shown embodiment, a first major surface 18a of the reinforcement layer is adhesively attached to backsheet layer 12, and a second major surface 18b of the reinforcement layer is appointed for adhesive bonding with tape tab 40. Reinforcement layer 18 in combination with the backsheet thereby provides a laminated target attachment zone against which tape tab 40 can be adhesively fastened. The composite is suitably arranged and configured such that the tape tab can be peeled from adhesive contact therewith substantially without delaminating the composite layers. In the illustrated embodiment, the layers are bonded together with an aggressive, pressure sensitive adhesive. Suitable adhesives are commercially available from various vendors, such as National Starch Co. located in Bridgewater, N.J.

In a particular aspect of the invention, reinforcement layer 18 has a substantially nonglossy, matte finish which extends over substantially its entire outwardly exposed surface area. In a particularly effective embodiment of the invention, the nonglossy reinforcement layer is composed of a substantially nonoriented polymer material. The nonglossy characteristic of the reinforcement layer may, for example, be evidenced by a 45° reflectivity value of not more than about 20. Preferably, the reflectivity value of reinforcement layer 18 is not more than about 10 and more preferably, the reflectivity value is not more than about 7, to provide a particularly pleasing appearance that coordinates well with the appearance of the matte finish of backsheet 12. If it is too glossy, reinforcement layer 18 can impart an undesired plastic appearance which may diminish the garment-like effect produced by the matte finish of the backsheet.

For the purposes of the present invention, the reflectivity value can be measured in accordance with standard procedure ASTM C346 employing a 45° Glossmeter apparatus. A suitable measurement apparatus is distributed by Pacific Scientific Co. located in Silver Spring, MD, and is designated model Glossgard II.

Reinforcement layer 18 should be suitably configured so as to avoid excessive stiffening of backsheet 12. Accordingly, the reinforcement layer material has a cantilever drape stiffness value of not more than about 6 cm. For improved performance, reinforcement layer 18 has a cantilever drape stiffness within the range of about 0.5-5 cm., and preferably has a drape stiffness of about 2.7 cm. A suitable technique for determining the cantilever drape stiffness value is U.S. Federal Test Method Standard No. 191, Procedure No. 5206.1.

To provide a desired operable amount of reinforcement, reinforcement layer 18 comprises a material having a tensile strength of at least about 15 MPa (about 2200 psi). Preferably the reinforcement layer material has a tensile strength of at least about 18 MPa (about 2600 psi). In the shown embodiment, the tensile strength of the reinforcement layer material is within the range of about 18–22 MPa (about 2600–3200 psi).

It is well recognized that the strength of the adhesive bond between the adhesive tape tab and the reinforcement layer material increases with the length of the dwell time over which the tape tab is continuously adhered to the reinforcement layer. As a result, when the dwell time is at least about 2 hours, a peeling removal of the tape tab from the reinforcement layer material alone at a peel rate of at least about 18 cm/sec can generate sufficient stresses to tear the reinforcement layer material.

To improve the effectiveness of the refastenable tape system, one aspect of the invention includes a reinforcement layer 18 which is bonded or otherwise attached to backsheet 12 to provide a composite laminate wherein the reinforcement layer substantially does not delaminate and separate from the backsheet when tape tab 40 is peeled from adhesive contact with the target securement zone on the reinforcement layer. In the shown embodiment of the invention, reinforcement layer 18 is adhesively bonded over substantially one entire facing surface to backsheet 12. A suitable adhesive for this purpose is a SBS (styrene-butadiene-styrene) based adhesive distributed by National Starch Co. of Bridgewater, N.J.

With reference to FIG. 3, reinforcement layer 18 extends over and covers at least the medial portion of a front waistband section of backsheet 12. Preferably, the reinforcement layer has a length dimension 60 which extends at least about 50% across the cross-directional width of the backsheet. Such a configuration provides a broad target zone against which to direct tape tab 40, and also, helps to spread out the stress produced by peeling the tape tab from adhesive contact with the backsheet. Reinforcement layer 18 also has a width dimension 62 of at least about 2.5 cm., and preferably has a width dimension of at least about 5.7 cm. to provide a reinforced target zone of effective dimensions.

The reinforced target zone, comprising reinforcement layer 18 bonded and laminated onto backsheet 12, has a composite load capacity capable of withstanding the peeling removal of adhesive tape tab 40 therefrom substantially without tearing or permanently deforming. In a particular aspect of the invention, the reinforced target zone composite has a tensile load capacity of at least about 31 N (about 7 lb-force), and preferably has a composite tensile load capacity of at least about 32 N (about 7.2 lb-force) to provide improved performance.

For the purposes of the present invention, the tensile load capacity of a material is determined with respect to a test sample of material having a width dimension of 1 inch (2.54 cm.). The load capacity is the tensile force at which the test sample first begins to yield and plastically deform.

A suitable material for reinforcement layer 18 is a nonoriented synthetic polymer material composed of a blend of polypropylenes or a blend of polypropylene and polyethylene. Suitable material is marketed by 3M Company of St. Paul, MN. Other suitable materials for the reinforcement layer can include, for example, a coated, nonwoven fibrous material.

In one embodiment of the invention, neither backsheet 12 nor reinforcement layer 18 is by itself capable of reliably withstanding the peel force generated by tape tab 40 without tearing. The combination of reinforcement layer 18 laminated with backsheet 12, however, is suitably constructed and arranged such that it can advantageously withstand the stresses imparted by a peeling removal of tape tab 40 from the composite, formed therefrom. During the peeling and separating operation, the composite, reinforced backsheet is capable of substantially avoiding delamination and tearing. As a result, tape tab 40 can be adhesively fastened, removed and refastened to reinforcement layer 18 a plurality of times without degrading the liquid barrier properties or appearance of backsheet 12.

The following example is given to provide a more detailed understanding of the present invention. The particular materials, amounts, proportions and parameters are exemplary and are not intended to specifically limit the scope of the invention.

EXAMPLE

A diaper contains an inner absorbent pad of bleached wood pulp, dried and fiberized into a layer of fluff and contoured to fit a selected product size. For a medium size product, the fluff pad weighs about 36 grams and has a basis weight of about 800 grams per square meter. The liquid permeable bodyside liner is composed of polypropylene fibers spunbonded together to provide a basis weight of about 20 gsm. The outer cover material of the diaper is comprised of a 1.3 mil (0.0013 inch) thick, white polyethylene sheet, which is liquid impermeable and has a basis weight of about 30 gsm. Additionally, the diaper includes a reinforcement layer bonded to the front outer surface of the cover material in the attachment tape landing area by means of a suitable SBS pressure sensitive adhesive. The reinforcement layer comprises a nonoriented, nonglossy, matte finish, polypropylene 3M material approximately 2.0 mils (0.002 inch) thick, which has a tensile strength of about 20 MPa (2900 psi) and a cantilever drape stiffness of about 2.2 cm. The reinforced area covers a zone on the diaper that extended about 5.7 cm down the face of the diaper, as measured from the top edge of the absorbent pad, and is centered with respect to the sides of the absorbent material. The length (60) of the reinforced area is approximately 25 cm. Attachment tape tabs (7.6 cm.×2.85 cm.) are used to secure the diaper and are composed of an approximately 4 mil thick, white polypropylene coated with an SBS pressure sensitive adhesive. Tape tabs are attached to each side of the diaper at the end of the diaper opposite from the reinforced zone such that the tabs can fasten onto the reinforced area when the diaper is in use.

Having thus described the present invention in rather full detail, it will be readily apparent to those having ordinary skill in the art that various changes and modifications can be made without departing from the spirit of the invention. All of such changes and modifications are contemplated as being within the scope of the invention, as defined by the subjoined claims.

We claim:

1. An article, comprising:
   an adhesive tape tab;
   a substrate layer composed of a material having a matte finish and having a tensile load capacity which is substantially unable to prevent tearing thereof when said tab is peeled from adhesive contact with the substrate layer; and
   a reinforcement layer, a first major surface of which is bonded to said substrate layer and a second major surface of which is appointed for adhesive bonding with said adhesive tab, said reinforcing layer providing a peel force value of at least about 11.7 N per inch of adhesive tab width when adhered to said adhesive tab, and said reinforcement layer having a matte finish and a tensile strength of at least about 15 MPa (about 2200 psi),
   said reinforcement layer and said substrate layer thereby forming a composite, reinforced substrate having a composite tensile load capacity capable of withstanding a peeling removal of said adhesive tab therefrom substantially without tearing.

2. An article as recited in claim 1, wherein said substrate layer is substantially liquid impermeable.

3. An article as recited in claim 1, wherein said substrate layer is elastomeric.

4. An article as recited in claim 1, wherein said substrate layer is a stretch-bonded-laminate material.

5. An article as recited in claim 1, wherein said substrate layer is vapor permeable and substantially liquid impermeable.

6. An article as recited in claim 1, wherein said reinforcement layer is a synthetic polymer film comprising a blend of polypropylenes.

7. An article as recited in claim 1, wherein said composite, reinforced substrate has a tensile load capacity of at least about 31 N (about 7-lb force) per inch of width.

8. An absorbent article, comprising:
 a backsheet layer which defines waistband sections at each longitudinal end thereof and defines an intermediate section interconnecting said waistband sections, said backsheet having a matte finish and a selected tensile strength;
 a liquid permeable liner sheet superposed in facing relation with said backsheet layer;
 an absorbent body located between said backsheet and said liner sheet;
 an adhesive tape tab connected to laterally opposed, side portions of at least one waistband section of said backsheet layer, said adhesive tab having a peel force value which is capable of tearing said backsheet when said tab is peeled therefrom; and
 a reinforcement layer, a first major surface of which is bonded to said backsheet layer and second major surface of which is appointed for bonding with said adhesive tab, said reinforcing layer providing a peel force value of at least about 117 N per inch of adhesive tab width when adhered to said adhesive tab, and said reinforcement layer having a matte finish and a tensile strength of at least about 15 MPa (about 2200 psi),
 said reinforcement layer and said backsheet layer thereby forming a composite, reinforced backsheet having a tensile load capacity capable of withstanding said peel force value from said adhesive tab substantially without tearing.

9. An article as recited in claim 8, wherein said backsheet layer is substantially liquid impermeable.

10. An article as recited in claim 8, wherein said backsheet layer is elastomeric.

11. An article as recited in claim 8, wherein said backsheet layer is a stretch-bonded-laminate material.

12. An article as recited in claim 8, wherein said backsheet layer is vapor permeable and substantially liquid impermeable.

13. An article as recited in claim 8, wherein said reinforcement layer is a synthetic polymer film comprising a blend of polypropylenes.

14. An article as recited in claim 8, wherein said composite, reinforced backsheet has a tensile load capacity of at least about 32 N (7.3 lb-force) per inch of width.

15. An article as recited in claim 1, wherein said reinforced substrate has a composite tensile load capacity capable of withstanding the peeling removal of said adhesive tab therefrom at a peel rate of at least about 18 cm/sec. substantially without tearing.

16. An article as recited in claim 1, wherein said reinforcement layer has a cantilever drape stiffness value of not more than about 6 cm.

17. An article as recited in claim 1, wherein said reinforcement layer has a cantilever drape stiffness value within the range of about 0.05–5 cm.

18. An article as recited in claim 1, wherein said reinforcement layer has a 45° reflective value of not more than about 20.

19. An article as recited in claim 1, wherein said reinforcement layer has a 45° reflectivity value of not more than about 10.

20. An article as recited in claim 1, wherein said reinforcement layer has a 45° reflectivity value of not more than about 7.

21. An article as recited in claim 8, wherein said reinforced substrate has a composite tensile load capacity capable of withstanding the peeling removal of said adhesive tab therefrom at a peel rate of at least about 18 cm/sec. substantially without tearing.

22. An article as recited in claim 8, wherein said reinforcement layer has a cantilever drape stiffness value of not more than about 6 cm.

23. An article as recited in claim 8, wherein said reinforcement layer has a cantilever drape stiffness value within the range of about 0.05–5 cm.

24. An article as recited in claim 8, wherein said reinforcement layer has a 45° reflectivity value of not more than about 20.

25. An article as recited in claim 8, wherein said reinforcement layer has a 45° reflectivity value of not more than about 10.

26. An article as recited in claim 8, wherein said reinforcement layer has a 45° reflectivity value of not more than about 7.

* * * * *

UNITED STATES PATENT AND TRADEMARK OFFICE
CERTIFICATE OF CORRECTION

PATENT NO. : 4,753,649
DATED : June 28, 1988
INVENTOR(S) : Patrick A. Pazdernik

It is certified that error appears in the above-identified patent and that said Letters Patent is hereby corrected as shown below:

IN THE CLAIMS:

Claim 8, column 11, line 33, delete "117" and substitute therefor -- 11.7 --.

Claim 17, column 12, line 20, delete "0.05" and substitute therefor -- 0.5 --.

Claim 18, column 12, line 22, delete "reflective" and substitute therefor -- reflectivity --.

Claim 23, column 12, line 40, delete "0.05" and substitute therefor -- 0.5 --.

Signed and Sealed this

Thirty-first Day of October, 1989

Attest:

DONALD J. QUIGG

*Attesting Officer*  *Commissioner of Patents and Trademarks*